(12) United States Patent
DiFoggio (10) Patent No.: US 7,886,821 B2
(45) Date of Patent: Feb. 15, 2011

(54) APPARATUS AND METHOD FOR DETERMINING FLUID PROPERTIES

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 115 days.

(21) Appl. No.: 12/019,452

(22) Filed: Jan. 24, 2008

(65) Prior Publication Data

US 2009/0188668 A1 Jul. 30, 2009

(51) Int. Cl.
*E21B 49/00* (2006.01)
(52) U.S. Cl. .......................... 166/264; 166/66; 356/326
(58) Field of Classification Search ................ 166/264, 166/66, 100; 356/326
See application file for complete search history.

(56) References Cited

U.S. PATENT DOCUMENTS

| | | | |
|---|---|---|---|
| 4,994,671 A | 2/1991 | Safinya et al. | |
| 5,303,775 A | 4/1994 | Michaels et al. | |
| 5,331,156 A | 7/1994 | Hines et al. | |
| 5,377,755 A | 1/1995 | Michaels et al. | |
| 5,411,106 A | 5/1995 | Maissa et al. | |
| 6,157,893 A | 12/2000 | Berger et al. | |
| 6,353,225 B1 | 3/2002 | Strzoda et al. | |
| 6,437,326 B1 | 8/2002 | Yamate et al. | |
| 7,207,216 B2 | 4/2007 | Meister et al. | |
| 7,214,933 B2 | 5/2007 | DiFoggio et al. | |
| 2004/0218176 A1 | 11/2004 | Shammal et al. | |
| 2006/0175547 A1 | 8/2006 | DiFoggio et al. | |
| 2006/0239330 A1 | 10/2006 | Yamate et al. | |
| 2007/0062696 A1 | 3/2007 | Wilson et al. | |
| 2007/0104616 A1* | 5/2007 | Keenan et al. | 422/100 |
| 2009/0153845 A1* | 6/2009 | DiFoggio | 356/133 |

FOREIGN PATENT DOCUMENTS

EP    1865147 A1    12/2007

OTHER PUBLICATIONS

International Search Report and Written Opinion, Mailed Sep. 23, 2009, International Application No. PCT/US2009/031499, International Search Report 4 pages, Written Opinion 7 pages.

* cited by examiner

*Primary Examiner*—William P Neuder
(74) *Attorney, Agent, or Firm*—Cantor Colburn LLP (57) ABSTRACT

A downhole fluid sample container includes a fluid sample container detachably coupled to a downhole sub, the fluid sample container having an internal chamber for receiving the downhole fluid. At least one semimetal (for example, silicon or germanium) window is coupled to the fluid sample container, the window being substantially transparent to electromagnetic energy wavelengths within a selected band. A method includes transmitting electromagnetic energy from an electromagnetic energy source to downhole fluid through at least one semimetal window in a container, receiving an electromagnetic energy response with a spectrometer, and estimating the downhole fluid property based at least in part on the electromagnetic energy response.

28 Claims, 4 Drawing Sheets

FIG. 4 a# APPARATUS AND METHOD FOR DETERMINING FLUID PROPERTIES

BACKGROUND

1. Technical Field

The present disclosure generally relates to formation fluid analysis and in particular to methods and apparatus for determining fluid properties of a fluid sample.

2. Background Information

Exploiting oil and gas reserves requires large capital investment placed at risk of poor producing reservoirs. Therefore, oil and gas companies attempt to gather as much information regarding subterranean formations as possible before and during drilling oil wells to help minimize the risks.

Information about the subterranean formations traversed by the borehole may be obtained by any number of techniques. Techniques used to obtain formation information include obtaining one or more fluid samples produced from the subterranean formations these samplings. Collected formation fluid samples may be contaminated by materials and fluids such as mud filtrates, drilling fluids and return fluids. Fluid samples are often retrieved from the borehole and tested in a rig-site or remote laboratory to determine properties of the samples, which properties are used to estimate formation properties. Modern fluid sampling also includes various downhole tests to estimate fluid properties while the fluid is downhole.

Determining fluid content provides valuable information regarding the viability of a particular reservoir and the content and quality of fluids produced.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is a downhole fluid sample container that includes a fluid sample container detachably coupled to a downhole sub, the fluid sample container having an internal chamber for receiving the downhole fluid. At least one semimetal window is coupled to the fluid sample container, the window being substantially transparent to electromagnetic energy wavelengths within a selected band.

An apparatus for estimating a property of a downhole fluid is disclosed that includes a fluid sample container that is detachably coupled to a downhole sub. The fluid sample container has an internal chamber for receiving the downhole fluid. At least one semimetal window is coupled to the fluid sample container, and the window is substantially transparent to electromagnetic energy wavelengths within a selected band. A spectrometer may be coupled to the semimetal window for estimating the downhole fluid property. At visible wavelengths, semimetals like silicon and germanium appear as shiny metals. However, semimetals will transmit both near-infrared and mid-infrared light whereas a traditional sapphire window cannot transmit most mid-infrared light such as mid-infrared light whose wavelength is longer than approximately 5 microns. In small diameters, semimetal windows are strong enough to withstand high downhole pressures even at high downhole temperatures. Semimetals are also very chemically inert so they are chemically resistant to downhole fluids. One can retrofit existing fluid collection tanks, which use a pair of sapphire windows, by replacing one sapphire window with a semimetal window. Then, near-infrared transmission spectra (1100-2500 nm) of the fluid inside can be obtained as before by transmitting light through one window, through the fluid, and through the other window. However, now it is also now possible to obtain mid-infrared attenuated reflectance spectra through the semimetal window, where the attenuated reflectance occurs at the interface of the semimetal window with the fluid. Ultraviolet experiments can be performed as before through the remaining sapphire window.

An exemplary method for estimating a property of a downhole fluid includes transmitting electromagnetic energy from an electromagnetic energy source to downhole fluid through at least one semimetal window in a container, receiving an electromagnetic energy response with a spectrometer, and estimating the downhole fluid property based at least in part on the electromagnetic energy response.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

Figure 1:
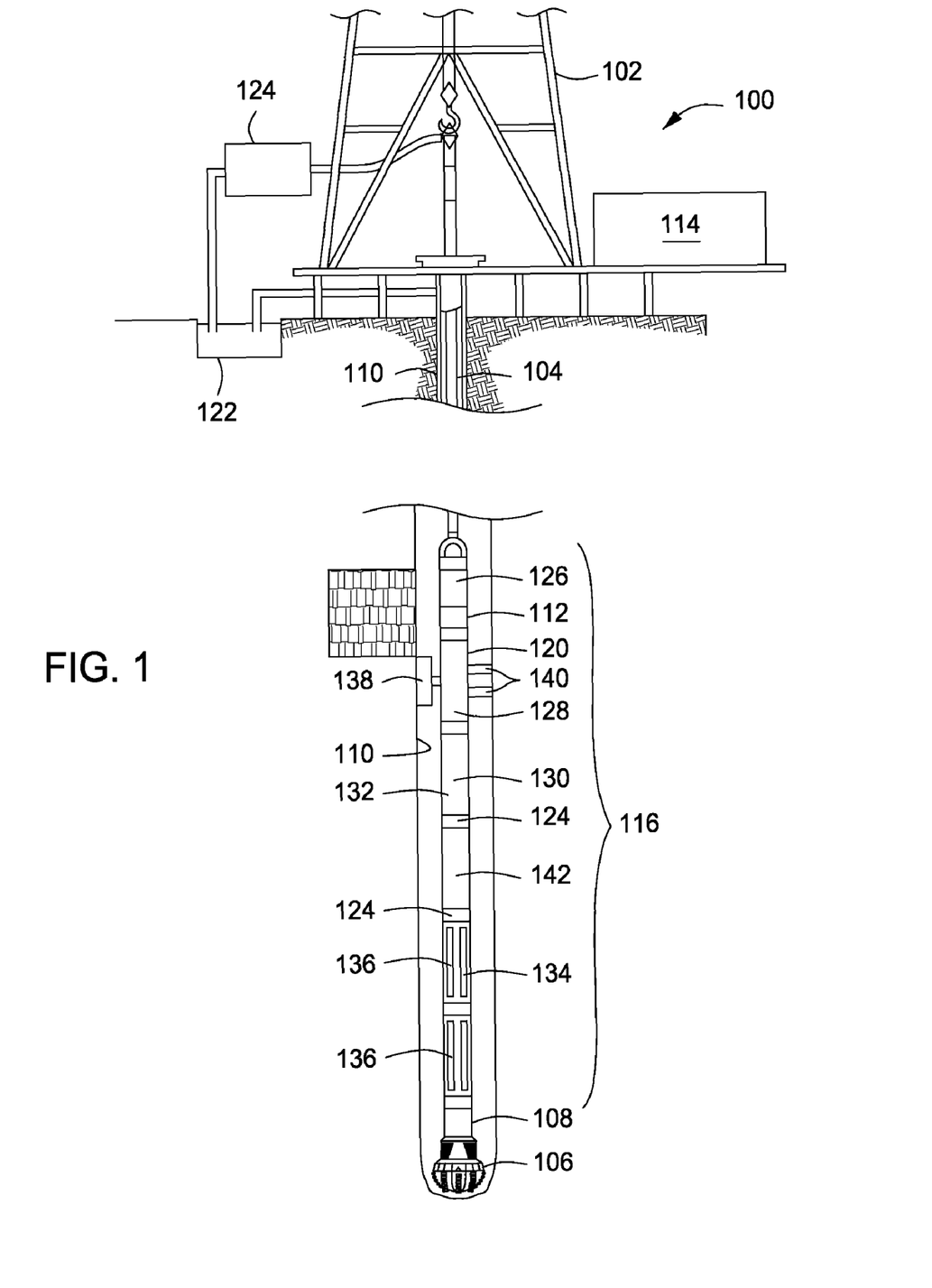
FIG. 1 illustrates a non-limiting example of a drilling system incorporating a fluid sample container for sampling downhole fluids.

FIG. 1 schematically illustrates a non-limiting example of a drilling system 100 in a measurement-while-drilling (MWD) arrangement according to several non-limiting embodiments of the disclosure. A derrick 102 supports a drill string 104, which may be a coiled tube or drill pipe. The drill string 104 may carry a bottom hole assembly (BHA) referred to as a downhole sub 116 and a drill bit 106 at a distal end of the drill string 104 for drilling a borehole 110 through earth formations.

Drilling operations according to several embodiments may include pumping drilling fluid or "mud" from a mud pit 122, and using a circulation system 124, circulating the mud through an inner bore of the drill string 104. The mud exits the drill string 104 at the drill bit 106 and returns to the surface through an annular space between the drill string 104 and inner wall of the borehole 110. The drilling fluid is designed to provide a hydrostatic pressure that is greater than the formation pressure to avoid blowouts. The pressurized drilling fluid may further be used to drive a drilling motor 108 and may provide lubrication to various elements of the drill string 104.

In the non-limiting embodiment of FIG. 1, the downhole sub 116 includes a formation evaluation tool 120. The formation evaluation tool 120 may include an assembly of several tool segments that are joined end-to-end by threaded sleeves or mutual compression unions 124. An assembly of tool segments appropriate for the present invention may include a power unit 126 that may include one or more of a hydraulic power unit, an electrical power unit or an electromechanical power unit. In the example shown, a formation fluid extractor 128 is coupled to the formation evaluation tool 120 below the power unit 126. The formation fluid extractor 128 comprises an extensible suction probe 138 that may be opposed by bore wall feet 140. Both, the suction probe 138 and the opposing feet 140 may be hydraulically or electromechanically extendable to firmly engage the well borehole wall. Construction and operational details of a suitable non-limiting fluid extraction tool 128 are more described by U.S. Pat. No. 5,303,775, the specification of which is incorporated herein by reference.

A large displacement volume motor/pump unit 130 may be provided below the formation fluid extractor 128 for line purging. A similar motor/pump unit 132 having a smaller displacement volume may be included in the tool in a suitable location, such as below the large volume pump, for quantitatively monitoring fluid received by the formation evaluation tool 120 via the formation fluid extractor 128.

In several embodiments to be described in further detail later, the formation evaluation tool 120 may include a spectrometer 142 located downhole, or a surface spectrometer may be used once the fluid container has been retrieved, for evaluating fluid received by the downhole sub 116. One or more detachable fluid sample containers 134 are included below the fluid pumps 130, 132 for retaining fluid samples received by the downhole sub 116. Each fluid container 134 may have several fluid sample tanks or internal fluid sample chambers 136. The fluid containers 134 will be described in more detail below with reference to FIG. 2.

Figure 2:
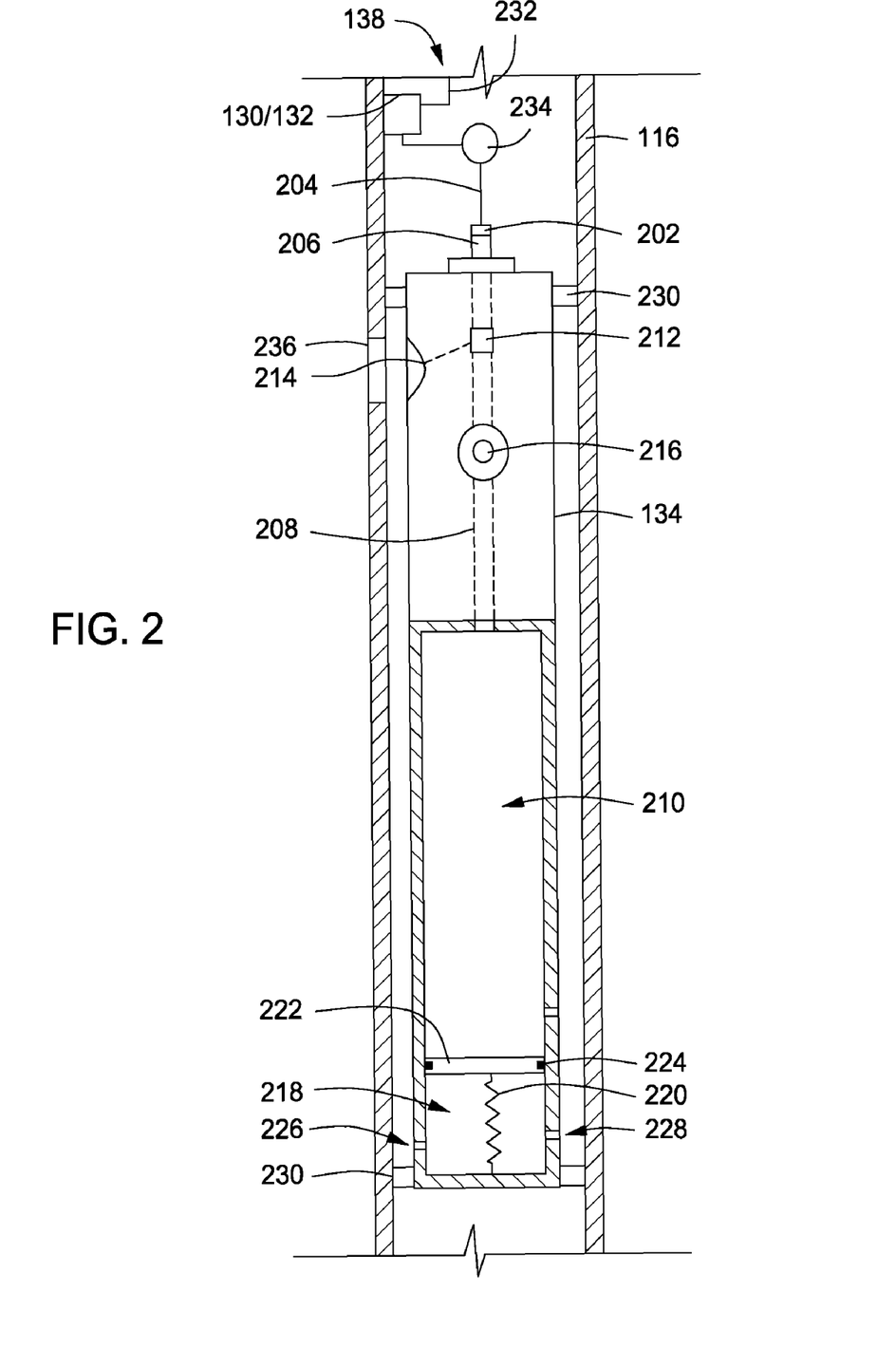
FIG. 2 is a non-limiting example of a fluid sample container according to the disclosure.

FIG. 2 illustrates a non-limiting example of a fluid sample container 134 that may be used in a while-drilling system as described above and shown in FIG. 1. The fluid sample container may also be used in a wireline-conveyed arrangement or a slickline arrangement using a downhole sub substantially similar to the downhole sub 116 described above and shown in FIG. 1.

The exemplary fluid sample container 134 shown in FIG. 2 includes a flow line connector 202 connected to a flow line 204 of the downhole sub 116. The exemplary fluid sample container 134 may further include a check valve 206 as shown coupled to the flow line connector 202 to provide fluid communication to a reduced volume section 208 of an internal sample chamber 210. A valve 212 is disposed in the reduced volume section 208 and is operable in the example shown by a valve actuator 214.

A window 216 is coupled to the fluid sample container 134 to provide electromagnetic energy communication with the reduced volume section 208. The window may be constructed using any rigid material capable of providing a pressure barrier for the fluid sample container 134 and that provides sufficient transmission of electromagnetic energy to fluid in the reduced volume section 202. In some non-limiting examples, the window 216 includes the semimetal silicon as a construction material. In other non-limiting embodiments, the window 216 may be constructed using germanium as a window material. In other non-limiting embodiments, the window 216 may be constructed using sapphire as a window material. In some examples, the fluid sample container 134 includes two or more windows. The windows of one or more embodiments include a combination of one or more silicon windows, germanium windows and one or more sapphire windows. A second window may be disposed in diametrical relationship to the window 216 for allowing electromagnetic energy to pass through fluid in the reduced volume section and exit via the second window where the reduced volume section has a fluid path length small enough so that fluid in the reduced volume section 208 does not attenuate the electromagnetic energy beyond the dynamic range of the spectrometer.

The reduced volume section 208 in one or more two-window transmission spectroscopy arrangements may be constructed having any suitable volume and path length that allows electromagnetic energy to pass through the fluid. In one embodiment, the path length of the reduced volume section 206 may be about 2 millimeters or less. The reduced volume section 208 in several one window and multi-window reflectance/refraction spectroscopy arrangements may be constructed having any suitable volume and path length that allows electromagnetic energy to interact with the fluid. In one embodiment, the path length of the reduced volume section 206 in a one-window arrangement is about 2 millimeters or less. In other embodiments, one window and multi-window reflectance/refraction spectroscopy arrangements may include a reduced volume section with a path length of more than 2 mm.

The fluid sample container 134 shown in FIG. 2 includes a pressure biasing device 218 in pressure communication with the internal sample chamber 210. The pressure biasing device 218, for example, may include a biasing spring 220 with pressure communication to the fluid sample chamber being provided by a piston 222. Fluid isolation between the biasing spring 220 and the internal sample chamber 210 may be effected using a suitable fluid seal 224, such as a polymer O-ring.

The biasing spring 220 may be any suitable device for providing pressure biasing. In several non-limiting embodiments, the biasing spring 220 may be a gas spring, a hydraulic spring, a mechanical spring, or any combination thereof. In one non-limiting example, the biasing spring 220 may be a gas spring using an inert gas such as Nitrogen. When using a gas spring, the fluid sampling container 134 may include a fluid inlet port 226 and a fluid outlet port 228 for charging and discharging the gas spring.

The biasing spring 220 may use a liquid. In some operational embodiments that will be described in more detail later, laboratory testing may include replacing a gas spring gas with water using the inlet port and outlet port for replacing the fluids.

The fluid sample container 134 may be detachably coupled to the downhole sub 116 according to several non-limiting embodiments of the present disclosure using one or more mounting members 230. The mounting members 230 may be any suitable mounting members that provide a detachable coupling between the downhole sub 116 and the fluid sample container 134. For example, the mounting members may include a threaded coupling so that the fluid sampling container may be easily inserted and removed from the downhole sub.

Referring now to FIGS. 1 and 2, a downhole sub 116 useful in several embodiments includes a flow line 232 leading from the fluid extractor 128 a sampling probe 138 shown in FIG. 1. One or more pumps 130, 132 may be used to convey fluid samples from the sampling probe 138 through the flow line 232 to a sub-carried valve 234. In some operational embodiments, a pressure differential between the formation and the internal sampling chamber 210 may be used to urge fluid into the chamber 210 without using a pump 130,132. In several operational embodiments, the sub-carried valve 234 is actuated downhole to open a flow path from the pump 130,132 to the fluid sample container 134 via the flow line connector 202. The check valve 206 may be used to ensure fluid flows in one direction toward the internal sample chamber 210 and provides a back-up function for the fluid sample container valve 212. In some embodiments, the fluid sample container valve actuator 214 may be a manual valve actuator such as a threaded actuator turned by hand using a tool accessing the manual valve actuator via a sub access port 236 in the downhole sub 116.

Figure 3:
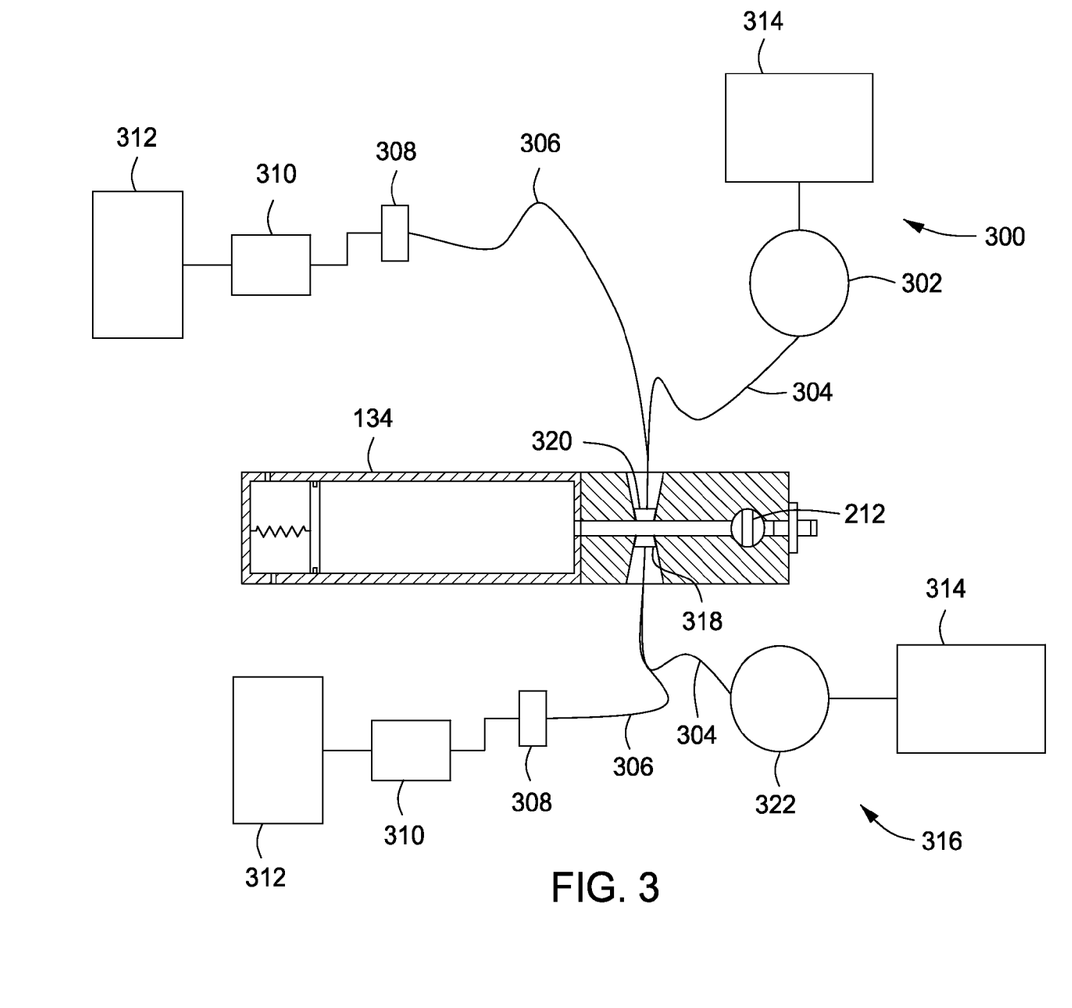
FIG. 3 is a non-limiting example of a fluid sample container according to the disclosure.

FIG. 3 schematically illustrates a non-limiting example of a test configuration according to the disclosure for estimating one or more properties of a downhole fluid within the fluid container 134. In one or more embodiments, the test configuration may include a spectrometer 300, and may further include a second spectrometer 316. One or both spectrometers 300, 316 may be incorporated into any of several wireline or while drilling tools, including the formation evaluation tool 120 described above and shown as a downhole spectrometer 142 in FIG. 1. One or both spectrometers 300, 316 in other embodiments may be incorporated into a surface laboratory configuration for testing downhole fluid within the fluid container in the surface laboratory. Laboratory test configurations may be used to test downhole fluids in substantially homogeneous phase where the downhole fluid sample has been maintained at or above a selected pressure, such as the bubble point pressure, using the pressure biasing device 218.

The spectrometer 300 in the example shown includes a light source 302. In several embodiments, the light source 302 may comprise an array of light sources. The light source 302 emits electromagnetic energy toward the fluid sample container 134 via one or more optical fibers 304. For the purposes of the present disclosure, the optical fibers 304 and associated connections for coupling the optical fibers to the container 134 may be considered a spectrometer interface coupled to the fluid sample container for providing communication between the container and the spectrometer. In some non-limiting embodiments, the optical fibers 304 may be replaced or used in combination with any suitable medium that conveys electromagnetic energy.

The optical fiber 304 in the example of FIG. 3 couples the light source 302 to a semimetal window 320. In several non-limiting embodiments, the semimetal window 320 is constructed at least in part using silicon. In several non-limiting embodiments, the semimetal window 320 is constructed at least in part using germanium. A second optical fiber 306 or other mid-infrared conduit couples the semimetal window 216 in the fluid sample container 134 to a photodetector 308 or other suitable detecting device. In one or more embodiments, the optical fiber 304 and second optical fiber may be part of an optical fiber bundle, where one or more fibers in the bundle carry energy to the window and one or more fibers carry energy reflected or refracted from the fluid sample.

The photodetector 308 may be used to receive light emitted from the light source 302 after the light interacts with the downhole fluid within the fluid sample container 134. Those skilled in the art with the benefit of the present disclosure will recognize that the photodetector 308 may be selected according to the particular light source type or test configuration used. Therefore, other test configurations utilizing detector types and/or configurations are within the scope of the disclosure without the need for further description. In one or more embodiments, the photodetector 308 comprises a single broadband photodetector responsive to light emitted from the light source 302. In other non-limiting embodiments, the photodetector 308 includes several photodetectors responsive to electromagnetic energy of selected wavelength or wavelength bands. The photodetector 308 provides an output signal indicative of the light received at the photodetector 308. In some cases, the photodetector output signal may be an analog electrical signal, so an analog-to-digital converter 310 may be used to convert the photodetector output signal into a digital signal that is received by an information processing device 312. The information processing device 312 may be any suitable processing device that includes a processor, memory, and interfaces sufficient to operate according to programmed instructions and/or instructions entered into the device for carrying out one or more analyses for estimating properties of the downhole fluid in the sample container. In laboratory embodiments, the information processing device 312 may comprise a computer such as a desk top, laptop, mainframe, network or any other computer suitable for operation in a surface environment. Non-limiting downhole configurations may include sufficient processing capability to carry out the analyses using instructions stored on a computer-readable medium.

The light emitted from the light source 302 may be modulated by a processor within the same information processing device 312 that receives the photodetector output or by a modulator in a separate information processing device 314 as shown.

In several embodiments, the light source 302 may include one or more broadband light sources such as an incandescent light source along with an optical filter to provide selected wavelengths. The light source 302 in some non-limiting embodiments may include one more light-emitting diodes (LED). The light source may also use one or more laser diodes. In other embodiments, the spectrometer 300 may include one or more light sources 302 that include a combination of light source types. The light source 302 in several embodiments emits electromagnetic energy in an infrared band of wavelength.

The second spectrometer 316 may be substantially similar to the spectrometer 300 coupled to the semimetal window 320. The spectrometer 316 may include a light source 322 that provides electromagnetic energy of wavelengths not transmitted to fluid within the fluid sample container 134 by the semimetal window 320. In one or more embodiments, the light source 322 emits electromagnetic energy in an ultraviolet band of wavelength. In several embodiments, an optical fiber 304 couples the second spectrometer light source 316 to a window 318 in the fluid sample container 134. A second optical fiber 308 couples the window 318 to a photodetector 308. The photodetector 308 may be coupled to an analog-to-digital converter 310, and the analog-to-digital converter, when used, may be coupled to an information processing device. Control of the emitted electromagnetic energy may be accomplished using a processor within the information processing device 312 or by using a separate processor 314 as discussed above with respect to the first spectrometer.

The second window 318 may be constructed using any suitable material that transmits electromagnetic to fluid within the fluid sample container 134. In several non-limiting embodiments, the window 318 coupled to the second spectrometer 316 includes sapphire as a window material. In some non-limiting examples, the window 318 may include one or both of the semimetals silicon and germanium as construction materials. In some embodiments, the first window 320 and/or the second window 318 may be constructed using a combination of materials. Separate input optical fibers 304 may be used to direct broadband energy or energy of selected wavelengths to particular window materials in windows having a combination of construction materials.

Figure 4:
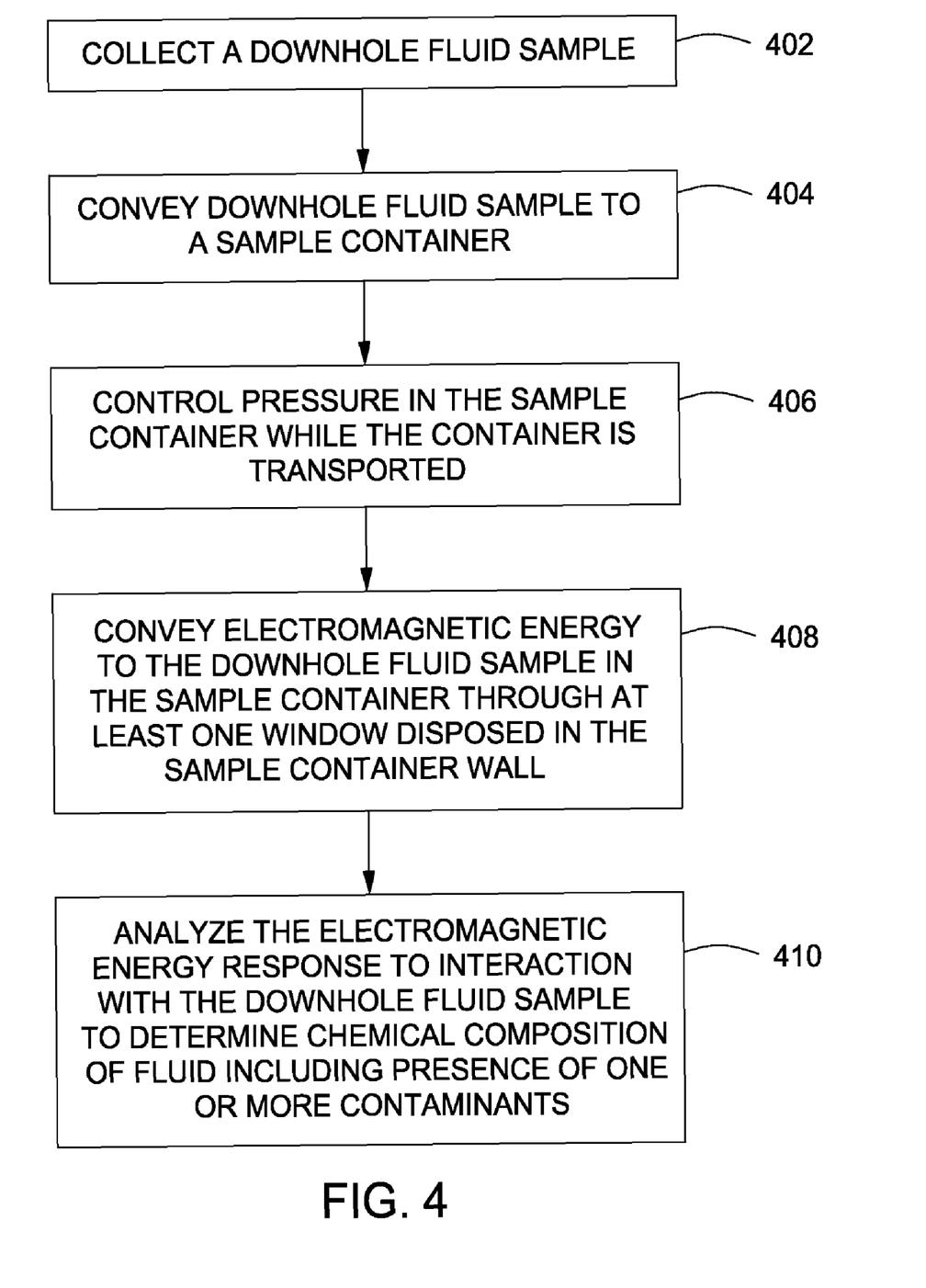
FIG. 4 illustrates an exemplary method for estimating downhole fluid properties.

Referring now to FIGS. 3 and 4, several non-limiting operational embodiments will be described. A detachable formation sample container 134 may be coupled to a downhole sub 116 of a wireline, slickline or drill string and conveyed to a subterranean formation of interest for collecting one or more samples of downhole fluids. A surface operator opens the sample container valve 234 before, after or as the sample container is assembled with the downhole sub 116. Once assembled, and with the sub-carried valve 136 in a closed position, the internal sample chamber 210 is evacuated to a selected pressure or is substantially sealed via the sub-carried valve 243 and check valve 206 at about 1 atmosphere of pressure. The sub is then conveyed into the borehole to the subterranean formation of interest. A fluid extraction device 128 is activated to form a hydraulic seal with the subterranean formation of interest and downhole fluid flows into the downhole sub 116 to collect a downhole fluid sample as noted in FIG. 4 at 402. The downhole fluid may include drilling fluid, borehole fluid, return fluid and/or pristine formation fluid. The sub-carried valve 234 is opened downhole to convey downhole fluid to the fluid container 134 as noted at 404 and to allow the downhole fluid to flow in the flow lines 232, 204 toward the internal sample chamber 210. In some examples, collecting and conveying the downhole fluid samples may include using pumps 130,132. In other examples, a pressure differential between the subterranean formation and the internal chamber 210 created by sealing the internal chamber during the surface assembly operations described above is used to collect and convey the downhole fluid. In some cases, a combination of using one or more pumps and a pressure differential may be used.

Pressure of the downhole fluid sample is controlled during and after collection via the pressure biasing device 218. In some examples, the pump 132 may be used to continue pumping fluid into the chamber 210 to pressurize the fluid in the chamber to a selected pressure higher than the formation pressure. Once a downhole fluid sample is collected and pressurizing, if used, is complete, the fluid volume within the sample container 143 is substantially sealed by closing the sub-carried valve. The check valve 206 operates as a back-up to the sub-carried valve 234 for maintaining pressure integrity within the sample container 134. Once sealed via the sub-carried valve and the check valve, the internal chamber pressure can be maintained or controlled using the pressure biasing device, while the sample container is transported within the borehole and to the surface.

At the surface, disassembly operations include closing the valve 212 via the sub access port 236 to seal the fluid volume in the sample chamber 210 and in the reduced-volume section 208. In the several embodiments disclosed, the fluid sample container is constructed to meet any applicable governmental transportation requirements for transporting pressurized hazardous materials. Thus, once the reduced-volume section valve 234 is closed, then the fluid sample container 134 may be detached from the downhole sub 116 and transported to a surface laboratory. During surface transportation, the pressure biasing device 218 continues to control pressure within the sample chamber 210.

Spectroscopy tests may be performed on the fluid in the sample container 134 without exposing the downhole fluid to ambient surface pressures by conveying electromagnetic energy to the downhole fluid via the window 216 as noted at 408. Then the electromagnetic energy response to interaction with the downhole fluid is analyzed using a spectrometer or other information processor to estimate properties of the downhole fluid as noted at 410. In several embodiments, the properties of interest estimated include fluid contamination. In several embodiments, contaminants include one or more compounds that provide electromagnetic energy reactions within the mid-infrared range. Some of these contaminants are the result of drilling fluids containing oil-based mud (OBM), which includes synthetic compounds such as esters and olefins. These compounds have distinctive mid-infrared spectrographic peaks due to their respective C═O and C═C bonds that do not occur naturally in formation fluids. With near-infrared spectroscopy, one cannot see these C═O and C═C bond vibrations because their overtone and combination bands are too weak, that is quantum mechanically unlikely.

In one non-limiting embodiment, the window 320 includes a sapphire material and the spectrometer 300 may comprise a pyroelectric array spectrometer for collecting mid-infrared spectra. The Mid infra-red spectra obtained will provide information useful in estimating the percent of OBM filtrate contamination. In one non-limiting example, the window 320 transmits electromagnetic wavelengths in the infrared band. In some non-limiting examples, the infrared band transmitted comprises a range of wavelengths of about 1 mm to about 750 nm. In some non-limiting examples, the window transmits electromagnetic energy in a mid-infrared band that includes wavelengths of about 5 microns to about 11 microns. Spectral analysis of peaks in these ranges may be used to determine OBM content and whether contaminants such as esters and olefins are present in a downhole fluid sample.

A UV Raman spectroscopy test configuration as illustrated in FIG. 3 using the second spectrometer 316 may be used in another embodiment of the estimating method. The window 318 may be made of sapphire and the method may include using UV Raman spectroscopy, which can be thought of as encoding mid-infrared spectral information, that is, molecular fundamental vibrational mode frequencies, on a UV carrier wave. In one embodiment, a UV spectrometer 316 is connected to the sample container 134 using a fluorescence fiber bundle 304. In this embodiment, UV light is conveyed via the bundle central optical fiber and Raman scattered light may be collected using the optical fibers 306 of the bundle surrounding the central optical fiber. The example of FIG. 3 shows incident light and return light on one side of the fluid container 134.

In other embodiments, transmission spectroscopy may be accomplished by detecting energy passing through the sample container from one window 318 to the window 320 diametrically disposed in the container 134. In some cases, windows 318,320 having multiple materials of construction may be used. For example, sapphire material on each side of the container may be used for transmission spectroscopy at wavelengths of sufficient energy to pass through the fluid. In some embodiments, a combination of reflection/refraction spectroscopy and transmission spectroscopy may be used in combination to estimate content of the downhole fluid.

The downhole fluid in the fluid container 134 may include one or more contaminants not indicative of pristine formation fluid. The contaminants may be due to drilling fluids entering the container along with formation fluid. In one or more embodiments, determining whether the fluid sample is contaminated by contaminants such as olefins and esters may be accomplished using a tool according to the present disclosure and examples described herein.

Having described above the several structural aspects of the disclosure, one skilled in the art will appreciate several particular embodiments useful in sampling downhole fluids and estimating one or more properties thereof.

In one particular embodiment, a downhole fluid sample container includes a fluid sample container detachably coupled to a downhole sub, the fluid sample container having an internal chamber for receiving the downhole fluid. At least one semimetal window is coupled to the fluid sample container, the window being substantially transparent to electromagnetic energy wavelengths within a selected band.

In another embodiment, an apparatus for estimating a property of a downhole fluid includes a fluid sample container that is detachably coupled to a downhole sub. The fluid sample container has an internal chamber for receiving the downhole fluid. At least one semimetal window is coupled to the fluid sample container, and the window is substantially transparent to electromagnetic energy wavelengths within a selected band. A spectrometer may be coupled to the semimetal window for estimating the downhole fluid property.

In one particular method embodiment, estimating a property of a downhole fluid includes transmitting electromagnetic energy from an electromagnetic energy source to downhole fluid through at least one semimetal window in a container, receiving an electromagnetic energy response with a spectrometer, and estimating the downhole fluid property based at least in part on the electromagnetic energy response.

In several particular embodiments, a downhole fluid sample container includes a semimetal window that is constructed using at least one of a silicon material and a germanium material. A second window that includes a sapphire material may be included in other particular embodiments.

In one particular embodiment, a downhole fluid sample container includes a pressure biasing device in pressure communication with an internal chamber for controlling pressure of the downhole fluid received in the internal chamber.

In several particular embodiments, a downhole fluid sample container includes a spectrometer interface coupled to a fluid sample container for providing communication between at least one semimetal window and a spectrometer.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

What is claimed is:

1. A container apparatus for containing a downhole fluid comprising:
    a fluid sample container that is detachably coupled to a downhole sub, the fluid sample container having an internal chamber for receiving the downhole fluid;
    at least one semimetal window that transmits electromagnetic energy wavelengths above a certain wavelength and reflects electromagnetic energy wavelengths below the certain wavelength, the at least one semimetal window being coupled to the fluid sample container, the window being substantially transparent to electromagnetic energy wavelengths within a selected band;
    wherein the at least one semimetal window is configured to withstand high downhole temperatures and high pressure differentials derived from high downhole pressures.

2. An apparatus according to claim 1, wherein the at least one semimetal window includes at least one of a silicon material and a germanium material.

3. An apparatus according to claim 1 further comprising a second window that includes a sapphire material.

4. An apparatus according to claim 1 further comprising a pressure biasing device in pressure communication with the internal chamber, the pressure biasing device controlling pressure of the downhole fluid received in the internal chamber.

5. An apparatus according to claim 1 further comprising a spectrometer interface coupled to the fluid sample container for providing communication between the at least one semimetal window and a spectrometer.

6. The apparatus according to claim 1, further comprising:
    a second window that includes a sapphire material and is configured to receive light transmitted through the at least one semimetal window;
    a first spectrometer interface coupled to the fluid sample container for providing communication between the at least one semimetal window and a first spectrometer; and
    a second spectrometer interface coupled to the fluid sample container for providing communication between the second window and a second spectrometer;
    wherein the apparatus is configured to perform a combination of reflection/refraction spectroscopy and transmission spectroscopy.

7. An apparatus for estimating a property of a downhole fluid comprising:
    a fluid sample container that is detachably coupled to a downhole sub, the fluid sample container having an internal chamber for receiving the downhole fluid;
    at least one semimetal window that transmits electromagnetic energy wavelengths above a certain wavelength and reflects electromagnetic energy wavelengths below the certain wavelength, the at least one semimetal window being coupled to the fluid sample container, the window being substantially transparent to electromagnetic energy wavelengths within a selected band; and
    a spectrometer coupled to the at least one semimetal window for estimating the downhole fluid property;
    wherein the at least one semimetal window is configured to withstand high downhole temperatures and high pressure differentials derived from high downhole pressures.

8. An apparatus according to claim 7, wherein the at least one semimetal window includes a silicon material.

9. An apparatus according to claim 7, wherein the selected band is an infrared band.

10. An apparatus according to claim 7, wherein the selected band is a mid-infrared band.

11. An apparatus according to claim 7, wherein the estimated downhole fluid property includes one or more contents of the downhole fluid.

12. An apparatus according to claim 11, wherein the one or more contents include oil-based muds.

13. An apparatus according to claim 11, wherein the one or more contents include at least one of olefins and esters.

14. An apparatus according to claim 7 further comprising a second window that includes a sapphire material.

15. An apparatus according to claim 7 further comprising a pressure biasing device in pressure communication with the internal chamber, the pressure biasing device controlling pressure of the downhole fluid received in the internal chamber.

16. An apparatus according to claim 7, wherein the spectrometer is disposed at least in part on the downhole sub.

17. An apparatus according to claim 7, wherein the downhole sub comprises at least one of a while-drilling sub, a wireline sub and a slickline sub.

18. A method for estimating a property of a downhole fluid inside a container, the method comprising:
    transmitting electromagnetic energy from an electromagnetic energy source to the downhole fluid through at least one semimetal window in the container, the semimetal window transmitting electromagnetic energy wavelengths above a certain wavelength and reflecting electromagnetic energy wavelengths below the certain wavelength;

receiving an electromagnetic energy response with a spectrometer; and estimating the downhole fluid property based at least in part on the electromagnetic energy response;

wherein the at least one semimetal window is configured to withstand high downhole temperatures and high pressure differentials derived from high downhole pressures.

19. A method according to claim 18, wherein the at least one semimetal window includes a silicon material.

20. A method according to claim 18, wherein transmitting electromagnetic energy through at least one semimetal window includes transmitting an infrared band.

21. A method according to claim 20, wherein the infrared band includes a mid-infrared band.

22. A method according to claim 18, wherein estimating the downhole fluid property includes estimating one or more contents of the downhole fluid.

23. A method according to claim 22, wherein the estimated one or more contents include oil-based muds.

24. A method according to claim 22, wherein the estimated one or more contents include at least one of olefins and esters.

25. A method according to claim 18 further comprising transmitting electromagnetic energy from an electromagnetic energy source to the downhole fluid through at least one second window in the container, the at least one second window including a sapphire material.

26. A method according to claim 18 further comprising controlling pressure of the downhole fluid received in the internal chamber using a pressure biasing device.

27. A method according to claim 18 further comprising:
receiving a second electromagnetic energy response with the spectrometer; and
estimating the downhole fluid property based at least in part on the second electromagnetic energy response.

28. A method according to claim 27, wherein the second electromagnetic energy response includes mid-infrared spectral information on a UV carrier wave.

* * * * *